(12) United States Patent
Liu

(10) Patent No.: US 9,060,984 B2
(45) Date of Patent: *Jun. 23, 2015

(54) RECOMBINANT HIV-1 ENVELOPE PROTEINS COMPRISING STABILIZING TWO-CYSTEINE MINI-DOMAINS IN GP41

(76) Inventor: George Dacai Liu, Redmond, WA (US)

( * ) Notice: Subject to any disclaimer, the term of this patent is extended or adjusted under 35 U.S.C. 154(b) by 416 days.

This patent is subject to a terminal disclaimer.

(21) Appl. No.: 13/279,250

(22) Filed: Oct. 22, 2011

(65) Prior Publication Data

US 2012/0107910 A1    May 3, 2012

Related U.S. Application Data

(60) Provisional application No. 61/408,574, filed on Oct. 30, 2010.

(51) Int. Cl.
*A61K 39/21* (2006.01)
*A61K 39/12* (2006.01)
*A61K 39/00* (2006.01)

(52) U.S. Cl.
CPC ............... *A61K 39/21* (2013.01); *A61K 39/12* (2013.01); *C12N 2740/16111* (2013.01); *A61K 2039/5258* (2013.01); *A61K 2039/53* (2013.01); *A61K 2039/543* (2013.01); *A61K 2039/545* (2013.01); *C07K 2319/00* (2013.01); *C07K 2319/03* (2013.01); *C07K 2319/72* (2013.01); *C12N 2740/16023* (2013.01); *C12N 2740/16034* (2013.01); *C12N 2760/16123* (2013.01); *C12N 2760/16134* (2013.01)

(58) Field of Classification Search
CPC ............... A61K 39/21; C07K 2319/03; C12N 2740/16034; C12N 2740/16023
See application file for complete search history.

(56) References Cited

PUBLICATIONS

Gallo, R. C., Nov. 2005, The end or the beginning of the drive to an HIV-preventive vaccine: a view from over 20 years, The Lancet 366:1894-1898.*
Walker, B. D., et al., 2008, Toward an AIDS vaccine, Science 320:760-764.*
McElrath, M. J., and B. F. Haynes, Oct. 2010, Induction of immunity to human immunodeficiency virus type-1 by vaccination, Immunity 33:542-554.*

* cited by examiner

*Primary Examiner* — Jeffrey Parkin
(74) *Attorney, Agent, or Firm* — George Dacai Liu

(57) ABSTRACT

The present invention provides a recombinant HIV Env antigenic protein, a virus-like particle and a recombinant HIV virus. The present invention further provides a vaccine comprising the recombinant HIV Env antigenic protein, the virus-like particle or recombinant HIV virus.

12 Claims, No Drawings

RECOMBINANT HIV-1 ENVELOPE PROTEINS COMPRISING STABILIZING TWO-CYSTEINE MINI-DOMAINS IN GP41

CROSS REFERENCE TO RELATED APPLICATIONS

The present application claims the priority of U.S. provisional application No. 61/408,574, filed on Oct. 30, 2010, entitled of "Recombinant envelope protein of human immunodeficiency virus (HIV) and vaccine containing the same", the disclosure of which is herein incorporated in its entirety.

FIELD OF THE INVENTION

The present invention relates to recombinant envelope proteins (Env) of human immunodeficiency (HIV) and vaccines comprising the same.

BACKGROUND OF THE INVENTION

Dreadfully infectious human immunodeficiency virus (HIV) is still causing grave consequences. Vaccines are considered as the most effective and economic means for prevention from and therapy of viral infections. Unfortunately, the viruses like HIV, are comprised of many serotypes, and undergo rapid antigenic changes; these make it a grave challenge to produce an effective vaccine for cross protections.

For HIV-1, however, there are already 33 million infected individuals who each harbor a substantial array of HIV-1 quasi-species, which results in an enormous number of variants that are simultaneously seeded and circulating in the human population. Providing protection against this vast array of potentially infectious isolates is a challenge of unprecedented magnitude in vaccine development. Not surprisingly, the classical vaccine approaches of chemical inactivation or live attenuation have not produced a broadly protective or safe HIV-1 vaccine. So far, a vaccine against HIV is not available.

SUMMARY OF THE INVENTION

One aspect of the present invention provides a recombinant HIV Env antigenic protein. In one embodiment, the recombinant HIV Env antigenic protein comprises an extracellular domain with major antigenic epitopes; a fusion peptide; and a membrane proximity external region (MPER); wherein at least one two-cysteine mini-domain selected from CxxC (SEQ ID NO 3), CxxxC (SEQ ID NO 4) or CxxxxC (SEQ ID NO 5) is present in the MPER, where x represents any amino acids; whereby when the recombinant HIV Env antigenic protein forms a trimer, the two cysteines in the MPER form a tandem disulfide bond belt, covalently tighting the trimer.

In another embodiment, the recombinant HIV Env antigenic protein further comprises a transmembrane domain (TMD); and a cytoplasmic domain (CPD); wherein the at least one two-cysteine mini-domain selected from CxxC (SEQ ID NO 3), CxxxC (SEQ ID NO 4) or CxxxxC (SEQ ID NO 5) is present in the MPER or TMD; whereby when the recombinant HIV Env antigenic protein forms a trimer, the two cysteines in the MPER or TMD form a tandem disulfide bond belt, covalently tightening the trimer.

In another embodiment of the recombinant HIV Env antigenic protein, the TMD is from one authentic HIV Env protein and the TMD is modified to contain the at least one two-cysteine mini-domain.

In another embodiment of the recombinant HIV Env antigenic protein, the TMD is an artificially synthetic peptide or derived from a non-Env protein forming trimers in its native configuration.

In another embodiment of the recombinant HIV Env antigenic protein, the recombinant HIV Env antigenic protein is encoded by a DNA sequence, and the DNA sequence is cloned into an in vivo expression vector; so that the recombinant HIV Env expression vector is used as a DNA vaccine against HIV infection.

In another embodiment of the recombinant HIV Env antigenic protein, the recombinant HIV Env antigenic protein is used in a vaccine against HIV infection.

Another aspect of the present invention provides a virus-like particle. In one embodiment, the virus-like particle comprises a recombinant HIV Env antigenic protein, wherein the recombinant HIV Env antigenic protein comprises an extracellular domain with major antigenic epitopes; a fusion peptide; a membrane proximity external region (MPER); a transmembrane domain (TMD); and a cytoplasmic domain (CPD); wherein at least one two-cysteine mini-domain selected from CxxC (SEQ ID NO 3), CxxxC (SEQ ID NO 4) or CxxxxC (SEQ ID NO 5) is present in the MPER or TMD, where x represents any amino acids; whereby when the recombinant HIV Env antigenic protein forms a trimer, the two cysteines in the MPER or TMD form a tandem disulfide bond belt, covalently tighting the trimer.

Another aspect of the present invention provides a recombinant influenza virus comprising a recombinant HIV Env antigenic protein.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Mannual*, third edition (Sambrook and Russel, 2001); *Animal Cell Culture* (R. I. Freshmey, ed., 1987); *Current Protocols in Molecular Biology* (F. M. Ausubel et al., eds., 1987, including supplements through 2001); *Current Protocols in Immunology* (J. E. Coligan et al., eds., 1991); *The Immunoassay Handbook* (D. Wild, ed., Stockton Press NY, 1994); *Methods of Immunological Analysis* (R. Masseyeff, W. H. Albert, and N. A. Staines, eds., Weinheim: VCH Verlags gesellschaft mbH, 1993).

The trimeric Env glycoprotein on HIV virion surfaces is the major antigenic target for neutralizing antibodies (Nabs). While Env glycoproteins from different strains have been reported with minor differences, their major structural domains are very similar. One exemplary encoding sequence for Env is shown in SEQ ID NO 1 and the translated Env protein is shown in SEQ ID NO 2. As shown in SEQ ID NO 2, the Env is comprised of 856 amino acids, where amino acids 1-511 forms gp120 containing the major antigenic epitopes and receptor binding domains, and amino acids 512-856 forms gp41. Initially, Env is produced as a highly glycosylated gp160 precursor, which is processed by a host protease into two subunits, gp120 and gp41. The two subunits remain associated by noncovalent interactions and form heterotrimeric spikes on the viral surfaces.

gp41 consists of ~345 amino acids divided into three major domains: extracellular region, also called ectodomain (aa 512 to 683; numbering is based on SEQ ID NO 2), the transmembrane domain (TMD) (aa 684 to 705), and the cytoplasmic tail (CT) (aa 705 to 856). In the ectodomain, there is a known membrane proximal external region (MPER) (aa 659 to 683). The TMD is composed of 22 aa and anchors Env into the lipid bilayer. It is highly conserved among different HIV-1 isolates and is thought to play a direct role in viral infection.

Previous studies have shown that monomeric pg120 immunogens have not elicited broadly reactive NAbs in animal models or humans, and thus attempts have focused on generating trimer immunogens that better mimic the native Env spike found on virions. It has, however, proven difficult to produce stable and conformationally homogeneous Env trimers. Strategies to modify Env immunogens have therefore been explored, including the removal of the cleavage site between gp120 and gp41, the incorporation of an intramolecular disulfide bond to stabilize cleaved gp120 and gp41 moieties, and the addition of trimerization motifs such as T4 bacteriophage fibritin "fold-on" (Fd) domain. It was reported that a recombinant Env trimer (gp140) was produced by fusing a T4 bacteriophage fibritin "fold-on" (Fd) domain to the C-terminal of MPER; the TMD and CT were deleted from the recombinant proteins. It was found that purified gp140 trimers with Ribi adjuvant elicited limited cross-clade neutralizing antibody responses. It is to be noted that Fd domain forms a trimer structure in a non-covalent manner.

While the development of an effective vaccine against HIV has been futile so far, the efforts of search for monoclonal antibodies (mAbs) that broadly neutralizing isolates of HIV have produced such a few mAbs, b12, 447-52D and 2G12 binding to gp120, whereas 2F5, Z13, 4E10 recognizing the MPER of gp41. These neutralizing mAbs inhibit infection by multiple genetic HIV-1 clades in vitro and prevent experimental infections in animal models with viruses bearing the envelope proteins from primary HIV-1 isolates. The discovery of broadly neutralizing mAbs has introduced the possibility of targeting their production in vivo by active immunization. This has proven difficult due to a number of factors including for example the structural complexities of the sites targeted by these mAbs. The vaccines based on the antibody epitope peptides were shown to stimulate a high titer, peptide-specific immune response; however, the resulting antisera were incapable of viral neutralization. In addition, the virus evades immune recognition by expressing a small number of viral spikes, shedding gp120 and masking neutralizing epitopes.

All previous studies suggest that the trimeric gp160, gp140 or gp41 does contain some antigenic epitopes that are shared by most or even all of HIV strains; unfortunately the cross reactive antibodies against the shared antigenic epitopes produced by immunization with current vaccines are too low to provide any meaningful protection against antigenic variants. If a HIV vaccine can elicit enough cross reactive antibodies against the shared antigenic epitopes, it will provide cross protection against all HIV variants (a universal vaccine). However, the challenge is how we could manipulate the HIV (ie., Env antigen) to achieve this goal.

The present invention hypothesized that the paucity of cross reactive antibodies in immunized or infected subjects might be due to less shared antigenic epitopes present in the current vaccines or during infection and further that the reason for the less shared antigenic epitopes present in the current vaccines is that natural Env structures do not offer sufficient stability to preserve the shared antigenic epitopes. Thus, if the stability of the Env structures can be increased, it is reasonably to expect the increases of the presence of the shared antigenic epitopes. However, the challenge is how to stabilize HA structures.

In our daily lives, a bundle of parallel materials such as bamboos and hays is held tightly by belts. Now the questions were whether Env contains any bundle of parallel structures and further whether any belt could be introduced into the bundle of parallel structures of Env if such bundle is present.

For the first question, the present invention analyzed the Env structure as described above. Gp41 contains many parallel helix structures in the fusion peptide, MPER and TMD. Early computer modeling suggested that the TMD of gp160 or gp41 adopts a single alpha-helix conformation; the peptide helix has a cylindrical configuration; thus the three helices from three TMD form a bundle of three parallel helices inside the Env timer; it provides the physical basis for introducing one or more belts covalently connecting all three Env monomers.

For the second question, the present invention recalled that the disulfide bond (S—S) formed by two cysteines can be formed between two peptides; for example IgG is a homodimer bounded by multiple inter-peptide disulfide bonds. However, one cysteine in the corresponding position of each of the three monomers in a HA trimer will allow the formation of one disulfide bond but leaving one SH group free. More critically, no circular belt around all three HA monomers is formed. In order to form a circular belt, the present invention explored whether it was feasible to introduce a pair of cysteines into each monomer so that a tandem of three disulfide bonds could be formed between the three monomers. As known, each turn in a helix contains 3.6 amino acids, where the pitch (advance per turn) is 0.54 nm, and the rise (advance per amino acid residue) is 0.15 nm. For a disulfide bond formed by two cysteines, the distance between their centers is 0.849 nm (two c-c bonds (0.154 nm per bond), two c-s bonds (0.17 nm per bond), and one s-s bond (0.201 nm)). The distance of 0.849 nm is about 1.57 pitch or 5.66 amino acids; it means that if two cysteines are not separated by more than 4 amino acids, a disulfide bond could be formed between two helices.

The present invention provides that the introduction of at least one pair of cysteines forming one of the three two-cysteine mini-domains ((CxxC (SEQ ID NO 3); CxxxC (SEQ ID NO 4); CxxxxC (SEQ ID NO 5)) into the TMD of Env (gp160, gp140 or gp41) enables the formation of a tandem disulfide bond belt between the three monomers, where the 'x' in the mini-domains is any amino acids as long as they do not break the helix structure, preferably A, L, M, F, E, Q, H, K and R in an artificially created mini-domain. Illustratively, the three disulfide bonds between three monomers (monomer 1 with 1C1 and 1C2; monomer 2 with 2C1 and 2C2; monomer 3 with 3C1 and 3C2) are 1C1-2C2, 2C1-3C2, and 3C1-1C2. This tandem disulfide bond belt tightly grips the three monomers together to form a highly stabilized trimer. This discovery is of great significance because any trimeric protein represented by Env could be manipulated to include at least one two-cysteine mini-domain so that the trimeric structure is stabilized by a covalent bond belt. When recombinant proteins of gp160, pg120 or gp41 are introduced with the tandem disulfide bond belt, their conformational structures are better stabilized, making the covalent gp160, gp120 or gp41 trimers as immunogens to more efficiently elicit broad neutralizing antibodies and further to be used as an effective vaccine against HIV. The recombinant Envs can be used as antigens for vaccines in the forms of recombinant proteins, VLP or viruses.

The introduction of a tandem disulfide bond belt into a recombinant protein of gp160 or gp41 can be achieved using any suitable molecular biological methods, for example point mutation, insertion or replacement; they are well established and known in the art. The exemplary embodiments of producing the recombinant Env protein include: (1) mutating two amino acid residues into cysteines in the TMD of gp160, gp140 or gp41 to form a two-cysteine mini-domain with a sequence selected from CxxC (SEQ ID NO 3), CxxxC (SEQ ID NO 4), or CxxxxC (SEQ ID NO 5); (2) inserting a two-cysteine mini-domain into the TMD of gp160, gp140 or gp41 as long as the insertion does not break the helix structure; (3) replacing a corresponding stretch of amino acids in the TMD or the whole TMD of gp160, gp140 or gp41 with one synthetic helical polypeptide containing with a two-cysteine mini-domain; (4) replacing a corresponding stretch of amino acids in the TMD or the entire TMD of gp160, gp140 or gp41 with the one from one natural molecule containing with a two-cysteine mini-domain for example CFFLC from H3TMD (SEQ ID NO 6); (5) fusing the entire extracellular domain of gp160, gp140 or gp41 to a sequence of TMD and CT of another protein, where the fused TMD contains at least one two-cysteine mini-domain. In some embodiments, the fused transmembrane domain can be from a protein that is intrinsically expressed as trimers; one example of such transmembrane domain is the one from influenza A virus H3 HA molecule that contains a CxxxC mini-domain in its transmembrane because H3 HA proteins are expressed as covalent trimers with three inter-molecular disulfide bonds. It is to be noted that the fusion in (5) would be advantageous when the antigenic extracellular domain of Env is desired to be represented in some vectors such as virus-like particles (VLP) or other virus particles.

In some embodiment, two or more two-cysteine mini-domains can be introduced into one Env recombinant protein.

Previously studies showed that the replacement of the TM region with another TM from other molecules such as influenza A virus H2 HA molecule did not affect its expression or incorporation into viral particles, even though the replacement showed some inhibition of viral infectivity. Other studies showed that the replacement of the TM region from cellular protein CD22 did not affect viral infectivity. All these demonstrated that the TMD region of gp160, gp140 or gp41 can be manipulated without necessarily changing their conformations. However, the previous replacement studies fail to suggest or teach that the TMD can be modified to stabilize the trimeric structure of Env proteins as disclosed in the present invention.

One embodiment of the present invention provides a recombinant HIV antigenic protein comprising a HIV receptor-binding extracellular domain of Env protein with major antigenic epitopes, a membrane proximal external region (MPER), a transmembrane domain (TMD) and a cytoplasmic domain (CPD), wherein at least one two-cysteine mini-domain selected from CxxC (SEQ ID NO 3), CxxxC (SEQ ID NO 4) or CxxxxC (SEQ ID NO 5) is present in the TMD. In some embodiments, authentic MPER, TMD or CPD from HIV Env proteins is modified to contain one or more two-cysteine mini-domains. In some embodiments, the MPER, TMD or CPD are derived from other trimeric molecules for example influenza virus HA molecules. In some embodiments, the MPER, TMD or CPD can be artificially synthetic peptides. The recombinant HIV antigenic protein can be expressed in any suitable system as long as the expression system produces effective recombinant HIV antigenic protein for vaccine use, for example yeast, insect cell or mammalian cell expression systems are suitable.

When a two-cysteine mini-domain is introduced to the MPER, the recombinant Env protein can be expressed as a soluble antigen with a covalent belt to reinforce the trimeric structure.

Another embodiment of the present invention provides an in vivo expression vector comprising an encoding sequence encoding a recombinant HIV antigenic protein, where the recombinant HIV antigenic protein comprises a HIV receptor-binding extracellular domain of Env protein, a membrane proximal external region (MPER), a transmembrane domain (TMD) and a cytoplasmic domain (CPD), wherein at least one two-cysteine mini-domain selected from CxxC (SEQ ID NO 3), CxxxC (SEQ ID NO 4) or CxxxxC (SEQ ID NO 5) is present in the MPER or TMD. In some embodiments, authentic MPER, TMD or CPD from HIV Env proteins is modified to contain one or more two-cysteine mini-domains. In some embodiments, the MPER, TMD or CPD are derived from other trimeric molecules for example influenza virus HA molecules. In some embodiments, the MPER, TMD or CPD can be artificially synthetic peptides. The expression vector is used as DNA vaccines; the exemplary expression vectors include lentivirus expression vector, adenovirus expression vector, adeno-associated virus expression vector or other mammalian expression vectors. For example, the encoding sequence for the HIV recombinant protein is cloned into a CMV/R expression vector for efficient expression in mammalian cells.

Another embodiment of the present invention provides a virus-like particle comprising a recombinant HIV antigenic protein comprising a HIV receptor-binding extracellular domain of Env protein, a membrane proximal external region (MPER), a transmembrane domain (TMD) and a cytoplasmic domain (CPD), wherein at least one two-cysteine domain selected from CxxC (SEQ ID NO 3), CxxxC (SEQ ID NO 4) or CxxxxC (SEQ ID NO 5) is present in the MPER or transmembrane domain. In some embodiments, the authetic TMD or CPD from HA proteins is modified to contain one or more two-cysteine mini-domains. In some embodiments, the TMD or CPD are derived from other trimeric molecules for example HIV Env molecules. In some embodiments, the TMD or CPD can be artificially synthetic. The HIV VLP can be generated by any suitable methods. In some embodiments, the HIV VLP is generated by co-expressing the recombinant HIV antigenic protein, influenza virus NA and M proteins when the Env extracellular domain is fused to the MPER/TM and CP of influenza virus HA, wherein the HA contains at least one two-cysteine mini-domain in its MPER/TM domains. The VLP can be generated by any suitable methods.

Another embodiment of the present invention provides a HIV recombinant virus comprising a recombinant HIV antigenic protein as described above. The HIV pseudovirus can be produced by any known methods. During the production of a vaccine using the HIV recombinant virus, the virus preparation can be made following the teachings of one accompanying application entitled "Viral vaccine and process for preparing the same", in which the proportion of the subpopulation of infectious viral particles in the virus preparation is optimized. In some embodiments, the HIV recombinant virus is a HIV pseudovirus for the sake of safety when the viral particles are sued for vaccine preparation.

The primary goal of the present invention is to provide a HIV vaccine that can elicit broad cross reactive immune responses. Thus, the recombinant Env, in vivo expression vector encoding the recombinant Env, the virus-like particles and the recombinant influenza virus can all be used in a vaccine. At the same time, they can also be used in many other ways for example as an antigen to produce the cross-reactive monoclonal antibodies or to identify the binding epitopes for monoclonal antibodies.

It is to be noted that many biotech applications are lengthy for stuffing extensive materials including methods and procedures that are well established and known in the art because the biotechnology was viewed with low predictability so that the examiners might raise the rejections failing to provide adequate details for one skilled in the art to practice the invention (lack of enablement). As a biotech researcher, the inventor of the present invention firmly believes that the biotechnology as a whole has advanced enough in the past thirty years that many basic procedures are well established and known, and more importantly the results are as predictable as that in the arts of mechanic and electronic engineering. For example, with a known virus and sequences, the DNA fragments of the virus shall be certainly obtained by PCR amplification; with a DNA fragment with known sequence, it shall be predictably subcloned into any vector including expression vectors in vitro and in vivo; with a cloned expression vector, the cloned gene shall be predictably expressed and purified; a virus-like particle can also be generated with known techniques; and a recombinant influenza virus can be rescued from plasmid systems such as reverse genetics. As a patent attorney, I strongly believe that biotech patent applications have come to the age when no more unnecessary materials are stuffed into an application, just as an electronic patent application never includes the description of the function of a capacitor or an amplifier. The elimination of the stuffed unnecessary materials helps to avoid the waste of time for both examiners and clients, and also makes the principles of the invention to be easily understood. In view of this, the known methods and materials are not included in this application.

As used herein, a "vaccine" is an antigenic preparation that is used to induce an immune response in individuals. A vaccine can have more than one constituent that is antigenic.

As used herein, "non-protein carriers" are carriers which are not proteins and can be used to achieve multimeric display of influenza matrix and/or nucleoprotein.

The term "microcarrier" refers to a particulate composition which is insoluble in water and which has a size of less than about 150, 120 or 100 um, more commonly less than about 50-60 um, and may be less than about 10 um or even less than about 5 um. Microcarriers include "nanocarriers," which are microcarriers have a size of less than about 1 um, preferably less than about 500 nm. Microcarriers include solid phase particles such particles formed from biocompatible naturally occurring polymers, synthetic polymers or synthetic copolymers, although microcarriers formed from agarose or cross-linkded agarose may be included or excluded from the definition of microcarriers herein as well as other biodigradable materials known in the art. Solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, and ferromagnetic and paramagnetic materials. Biodegradable solid phase microcarriers may be formed from polymers which are degradable (e.g., poly(lactic acid), poly(glycolic acid) and copolymers thereof, such as poly(D, L-lactide-co-glycolide) or erodible (e.g., poly(ortho esters such as 3,9-diethylidene-2,4,8,10-tetraoxaspiro[5,5]undecane (DETOSU) or poly(anhydrides), such as poly(anhydrides) of sebacic acid) under mammalian physiologically conditions. Microcarriers are typically spherical in shape, but microcarriers which deviate from spherical shape are also acceptable (e.g., ellipsoidal, rod-shaped, etc.). Due to their insoluble nature, some solid phase microcarriers are filterable from water and water-based (aqueous) solutions (e.g., using a 0.2 micron filter). Microcarriers may also be liquid phase (e.g., oil or lipid based), such as liposomes, iscoms (immune-stimulating complexes, which are stable complexes of cholesterol, phospholipid and adjuvant-active saponin) without antigen, or droplets or micelles found in oil-in-water or water-in-oil emulsions, such as MF59. Biodegradable liquid phase microcarriers typically incorporate a biodegradable oil, a number of which are known in the art, including squalene and vegetable oils. The term "nonbiodegradable", as used herein, refers to a microcarrier which is not degraded or eroded under normal mammalian physiological conditions. Generally, a microcarrier is considered nonbiodegradable if it no degraded (i.e., loses less than 5% of its mass or average polymer length) after a 72 hour incubation at 37° C. in normal human serum.

An "individual" or "subject" is a mammal including but not limited to, humans, non-human primates, farm animals, sport animals, experimental animals, rodents (e.g., mice and rats) and pets.

An "effective amount" or a "sufficient amount" of a substance is that amount sufficient to effect a desired biological effect, such as beneficial results, including clinical results, and as such, an "effective amount" depends upon the context in which it is being applied. In the context of this invention, an example of an effective amount of a composition comprising the desired antigen is an amount sufficient to induce an immune response in an individual. An effective amount can be administered in one or more administrations.

"Stimulation" of an immune response, such as humoral or cellular immune response, means an increase in the response, which can arise from eliciting and/or enhancement of a response.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of infection, stabilized (i.e., not worseing) state of infection, amelioration or palliation of the infectious state, and remission (whether partial or total), whether detectable or undetectable. "Treatment" can also mean prolonging survival as compared to expected survival if not receiving treatment.

According to the present invention, a "dose" of a vaccine composition, is a quantity of vaccine composition that is administered at a particular point in time. A "dose" may also be a quantity of vaccine composition that is gradually administered to an animal using an extended release formulation and/or apparatus. In certain embodiments of the present invention, two or more doses of the vaccine composition are administered to an animal at different time points.

According to the present invention, an "immunologically-effective amount" of a HIV antigen (e.g., recombinant Env protein) is an amount of recombinant Env protein which will induce complete or partial immunity in a treated animal against subsequent challenge with a virulent strain of HIV virus. Complete or partial immunity can be assessed by observing, either qualitatively or quantitatively, the clinical symptoms of HIV virus infection in a vaccinated animal as compared to an unvaccinated animal after being challenged with virulent strains of HIV virus. Where the clinical symptoms of HIV virus infection in a vaccinated animal after challenge are reduced, lessened or eliminated as compared to the symptoms observed in an unvaccinated animal after a similar or identical challenge, the amount of recombinant protein that was administered to the vaccinated animal is regarded as an "immunologically-effective amount".

A "cross-protective immune response" is one which protects against infection by a virus strain which is not identical to the one used to elicit the response.

As will be understood in the art, an "adjuvant" means one or more substances that enhance the immunogenicity and/or efficacy of a vaccine composition. Non-limiting examples of suitable adjuvants include squalane and squalene (or other oils of animal origin); block copolymers; detergents such as Tween-80; Quil A, mineral oils such as Drakeol or Marcol, vegetable oils such peanut oil; *Corynebacterium*-derived adjuvants such as *Corynebacterium parvum; Propionibacterium*-derived adjuvants such as *Propionibacterium acne; Mycobacterium bovis* (Bacille Calmette and Guerin or BCG); interleukins such as interleukin 2 and interleukin 12; monokines such as interleukin 1; tumor necrosis factor; interferons such as gamma interferon; surface active substances such as hexadecylamine, octadecylamine, octadecyl amino acid esters, lysolecithin, dimethyldioctadecylammonium bromide, N,N-dicoctadecyl-N',N'bis)2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; combinations such as saponin-aluminium hydroxide or Quil-A aluminium hydroxide; liposomes; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

A therapeutic composition of the present invention can be formulated in an excipient that the object to be treated can tolerate. Examples of such excipients include water, saline, Ringer's solution, dextrose solution, Hank's solution, and other aqueous physiologically balanced salt solutions. Excipients can also contain minor amounts of additives, such as substances that enhance isotonicity and chemical or biological stability. Examples of buffers include phosphate buffer, bicarbonate buffer, and Tris buffer, while examples of stabilizers include A1/A2 stabilizer, available from Diamond Animal Health, Des Moines, Iowa.

Acceptable protocol to administer therapeutic compositions in an effective manner includes individual dose size, number of doses, frequency of dose administration, and mode of administration. Determination of such protocols can be accompanied by those skilled in the art, and examples are disclosed herein.

Administering or administer is defined as the introduction of a substance into the body of an individual and includes oral, nasal, ocular, rectal, vaginal and parenteral routes. Compositions may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN) or orally.

The dose administered to a patient, in the context of the present invention, should be sufficient to effect a beneficial response in a patient over an appropriate period of time. The quantity of agents to be administered may depend on the subject to be treated inclusive of the age, sex, weight and general health condition thereof, factors that will depend on the judgment of the practitioner.

Immunotherapeutic compositions of the invention may be used to prophylactically or therapeutically immunize animals such as humans. However, other animals are contemplated, preferably vertebrate animals including domestic animals such as livestock and companion animals.

The vaccine may be used in combination with others; for example, priming with an attenuated vaccine follows with a boost using the inactivated vaccine.

The invention encompasses all pharmaceutical compositions comprising an antigen, an adjuvant, and a pharmaceutically acceptable carrier.

Pharmaceutically acceptable carriers preferred for use in the present invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose", and the like. Preservatives and other additives may also be present such as, for example, antimicrobials, antioxidants, chelating agents, and inert gases and the like.

EXAMPLES

The following examples are provided for the sole purpose of illustrating the principles of the present invention; they are by no means intended as limitations of the present invention.

I. Recombinant HIV Env Antigenic Protein Expression Vector pcDNA 3.1 and pFastBac Dual were from Invitrogen.

The DNA fragments encoding the extracellular domain of Env (SEQ ID NO 2) (gp140) and the TMD of H3 HA (SEQ ID NO 6) were separated amplified and ligated, where the protease site in the extracellular domain was eliminated by site-directed mutation. The ligated Env-H3TMD was cloned into pcDNA 3.1 for being used as DNA vaccine and pFastBac Dual for making VLP.

II. Animal Studies 6-8 weeks-old Balb/C mice (5 per group) were intramuscularly immunized with 30 ug three times (sera were collected one week after immunization), and followed by mucosal immunization (nose) three times with VLP (sera were collected two weeks after immunization). ELISA results showed that the group immunized with pcDNA-gp140TM had the highest titer against HIV VLP. It demonstrated that the introduction of the H3TMD with a two-cysteine mini-domain enhanced its antigenicity.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A recombinant HIV Env antigenic protein, comprising:
an extracellular domain with major antigenic epitopes;
a fusion peptide; and
a membrane proximity external region (MPER);
wherein at least one two-cysteine mini-domain selected from CxxC (SEQ ID NO 3), CxxxC (SEQ ID NO 4) or CxxxxC (SEQ ID NO 5) is present in the MPER, where x represents any amino acids as long as they do not break the helix structure.

2. A recombinant HIV Env antigenic protein comprising:
an extracellular domain with major antigenic epitopes;
a fusion peptide;
a membrane proximity external region (MPER);
a transmembrane domain (TMD); and
a cytoplasmic domain (CPD);
wherein the at least one two-cysteine mini-domain selected from CxxC (SEQ ID NO 3), CxxxC (SEQ ID NO 4) or CxxxxC (SEQ ID NO 5) is present in the MPER or TMD, where x represents any amino acids as long as they do not break the helix structure.

3. The recombinant HIV Env antigenic protein of claim 2, wherein the TMD is from one authentic HIV Env protein and the TMD is modified to contain the at least one two-cysteine mini domain.

4. The recombinant HIV Env antigenic protein of claim 2, wherein the TMD is an artificially synthetic peptide or derived from a non-Env protein forming trimers in its native configuration.

5. The recombinant HIV Env antigenic protein of claim 1, wherein the recombinant HIV Env antigenic protein is encoded by a DNA sequence, and the DNA sequence is cloned into an in vivo expression vector.

6. The recombinant HIV Env antigenic protein of claim 2, wherein recombinant HIV Env antigenic protein is encoded by a DNA sequence, and the DNA sequence is cloned into the an in vivo expression vector.

7. The recombinant HIV Env antigenic protein of claim 1, wherein the recombinant HIV Env antigenic protein is used in an immunogenic composition against HIV infection.

8. The recombinant HIV Env antigenic protein of claim 2, wherein the recombinant HIV Env antigenic protein is used in an immunogenic composition against HIV infection.

9. The recombinant HIV Env antigenic protein of claim 1, wherein the recombinant HIV Env antigenic protein is incorporated into a virus-like particle.

10. The recombinant HIV Env antigenic protein of claim 2, wherein the recombinant HIV Env antigenic protein is incorporated into a virus-like particle.

11. The recombinant HIV Env antigenic protein of claim 1, wherein the recombinant HIV Env antigenic protein is incorporated into a recombinant HIV virus.

12. The recombinant HIV Env antigenic protein of claim 2, wherein the recombinant HIV Env antigenic protein is incorporated into a recombinant HIV virus.

* * * * *

SEQUENCE LISTING

<160> NUMBER OF SEQ ID NOS: 6

<210> SEQ ID NO 1
<211> LENGTH: 2571
<212> TYPE: DNA
<213> ORGANISM: Human immunodeficiency virus
<300> PUBLICATION INFORMATION:
<308> DATABASE ACCESSION NUMBER: AB253428.1
<309> DATABASE ENTRY DATE: 2006-09-15
<313> RELEVANT RESIDUES IN SEQ ID NO: (1)..(2571)

<400> SEQUENCE: 1

| | | | | | |
|---|---|---|---|---|---|
| atgagagtga | tggggataga | gaggaattat | ccttgctggt | ggacatgggg | gattatgatc | 60 |
| ttggggatga | taataatttg | taatactgca | gaaaacttgt | gggttactgt | ctactatggg | 120 |
| gtacctatat | ggaaggatgc | aaataccacc | ttatttttgtg | catcagatgc | gaaagcatat | 180 |
| gacacagaag | tgcataatgt | ctgggctacg | catgcctgtg | tacctacaga | ccccagccca | 240 |
| caagaactaa | aaatggaaaa | tgtgacagaa | gagtttaaca | tgtggaaaaa | taacatggta | 300 |
| gaacagatgc | atacagatat | aatcagtcta | tgggaccaaa | gcctaaaacc | atgtgtacag | 360 |
| ttaaccccctc | tctgcgttac | tttagattgt | agctataaca | tcaccaataa | tatcaccaat | 420 |
| agcatcacca | atagctcagt | taacatgaga | gaagaaataa | aaaactgctc | tttcaatatg | 480 |
| accacagaat | taagggataa | gaatcggaag | gtatattcac | ttttttataa | acttgatgta | 540 |
| gtacaaatta | ataatggtaa | taacagtagt | aatctgtata | gattaataaa | ttgtaatacc | 600 |
| tcagccctta | cacaggcttg | tccaaaggta | acctttgagc | caattcccat | acattattgt | 660 |
| gccccagctg | gttatgcgat | tctaaaatgt | aatgataagg | agttcaatgg | aacagggcta | 720 |
| tgcaagaatg | tcagcacagt | acaatgcaca | catggaatca | ggccagtagt | atcaactcaa | 780 |
| ctgctgttaa | atggcagttt | agcagaagga | aaggtaatga | ttagatctga | aaatatcaca | 840 |
| aacaatgtca | aaacataat | agtacaactt | aacgagtctg | taacaattaa | ttgtaccaga | 900 |
| cctaacaata | tacaagaag | aagtgtacgt | ataggaccag | gacaaacatt | ctatgcaaca | 960 |
| ggtgatataa | tagggatat | aagacaagca | cattgtaatg | tcagtgggtc | acaatggaat | 1020 |
| aaaactttac | caggtagt | tgaacaatta | agaaaatatt | ggaacaacaa | tacaataatc | 1080 |
| tttaatagct | cctcaggagg | ggatttagaa | attacaacac | atagttttaa | ttgtggagga | 1140 |
| gaattttttct | attgtaatac | atcaggcctg | tttaatagta | cttgggtaaa | tggcactgcc | 1200 |
| agcatagaaa | atggcactat | aactctccca | tgcagaataa | agcaaattat | aaatatgtgg | 1260 |
| cagagagtag | gacaagcaat | atatgcccct | cccatccaag | gagtaataag | gtgtgtatca | 1320 |
| aacattacag | gactaatatt | aacaagagat | ggtgggggta | tagcaatga | aaatgaaacc | 1380 |
| ttcagacctg | gaggaggaga | tatgagggac | aattggagaa | gtgaattata | taagtataaa | 1440 |
| gtagtaaaaa | ttgaaccact | aggagtagca | cccaccaagg | caaggagaag | agtggtggag | 1500 |
| agagaaaaaa | gagcagttac | actgggagct | gtattcattg | ggttcttagg | aacagctgga | 1560 |
| agcacaatgg | gcgcggcgtc | aataacgctg | acggtacagg | ccagaaaatt | attatctggc | 1620 |
| atagtgcaac | agcaaagcaa | tttgctgagg | gctatagagg | ctcaacagca | tctgttgaaa | 1680 |
| ctcactgtct | gggcattaa | acagctccag | gcaagagtcc | tggctgtgga | aagatacta | 1740 |
| agggatcaac | agctcctagg | aatttgggc | tgctctggaa | aactcatctg | ccccactaat | 1800 |
| gtgccctgga | actctagctg | gagtaataaa | tctctagatg | aaatatggga | taacatgacc | 1860 |
| tggctgcaat | gggataaaga | aattagcaat | tacacaatca | aaatatatga | gctaattgaa | 1920 |
| gaatcgcaga | tccagcagga | aaggaatgaa | aaagacttat | tggaattgga | caagtgggca | 1980 |

-continued

```
agtctgtgga attggtttga catatcaaaa tggctgtggt atataaaaat atttataatg    2040
atagtaggag gcctaatagg attaagaata gttttttgctg tgctttctgt aataaataga    2100
gttaggcagg gatactcacc cctatcgttt cagacccata ccccgaaccc aaggggactc    2160
gacaggcccg gaagaatcga agaagaaggt ggagagcaag acagaggcag atcgatacgc    2220
ttagtgagcg ggttcttagc acttgcctgg gacgacctgc ggaacctgtg cctcttcagc    2280
taccaccgat tgagagactt catcttgatt gcagcgagga ctgtggaact tctgggacac    2340
agcagtctca aggggttgag actggggtgg gaaggactca agtatctggg gaatctcctg    2400
ttgtattggg gtcgggaact aaaaattagt gctattaatt tgcttgatac catagcaata    2460
gcagtagctg gctggacaga tagggttata gaaacagtac aaaggcttgg tagagctatt    2520
ctcaacatac ctagaagaat caggcagggc ttcgaaaggg ctttactata a             2571
```

<210> SEQ ID NO 2
<211> LENGTH: 856
<212> TYPE: PRT
<213> ORGANISM: Human immunodeficiency virus
<300> PUBLICATION INFORMATION:
<308> DATABASE ACCESSION NUMBER: BAF31403.1
<309> DATABASE ENTRY DATE: 2006-09-15
<313> RELEVANT RESIDUES IN SEQ ID NO: (1)..(856)

<400> SEQUENCE: 2

```
Met Arg Val Met Gly Ile Glu Arg Asn Tyr Pro Cys Trp Trp Thr Trp
1               5                   10                  15

Gly Ile Met Ile Leu Gly Met Ile Ile Cys Asn Thr Ala Glu Asn
            20                  25                  30

Leu Trp Val Thr Val Tyr Tyr Gly Val Pro Ile Trp Lys Asp Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Ser Pro
65                  70                  75                  80

Gln Glu Leu Lys Met Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Gln Leu Thr Pro Leu Cys Val Thr Leu
        115                 120                 125

Asp Cys Ser Tyr Asn Ile Thr Asn Asn Ile Thr Asn Ser Ile Thr Asn
    130                 135                 140

Ser Ser Val Asn Met Arg Glu Glu Ile Lys Asn Cys Ser Phe Asn Met
145                 150                 155                 160

Thr Thr Glu Leu Arg Asp Lys Asn Arg Lys Val Tyr Ser Leu Phe Tyr
                165                 170                 175

Lys Leu Asp Val Val Gln Ile Asn Asn Gly Asn Asn Ser Ser Asn Leu
            180                 185                 190

Tyr Arg Leu Ile Asn Cys Asn Thr Ser Ala Leu Thr Gln Ala Cys Pro
        195                 200                 205

Lys Val Thr Phe Glu Pro Ile Pro Ile His Tyr Cys Ala Pro Ala Gly
    210                 215                 220

Tyr Ala Ile Leu Lys Cys Asn Asp Lys Glu Phe Asn Gly Thr Gly Leu
225                 230                 235                 240

Cys Lys Asn Val Ser Thr Val Gln Cys Thr His Gly Ile Arg Pro Val
```

-continued

```
            245                 250                 255
Val Ser Thr Gln Leu Leu Asn Gly Ser Leu Ala Glu Gly Lys Val
            260                 265                 270

Met Ile Arg Ser Glu Asn Ile Thr Asn Asn Val Lys Asn Ile Ile Val
            275                 280                 285

Gln Leu Asn Glu Ser Val Thr Ile Asn Cys Thr Arg Pro Asn Asn Asn
    290                 295                 300

Thr Arg Arg Ser Val Arg Ile Gly Pro Gly Gln Thr Phe Tyr Ala Thr
305                 310                 315                 320

Gly Asp Ile Ile Gly Asp Ile Arg Gln Ala His Cys Asn Val Ser Gly
                325                 330                 335

Ser Gln Trp Asn Lys Thr Leu His Gln Val Glu Gln Leu Arg Lys
            340                 345                 350

Tyr Trp Asn Asn Asn Thr Ile Ile Phe Asn Ser Ser Gly Gly Asp
            355                 360                 365

Leu Glu Ile Thr Thr His Ser Phe Asn Cys Gly Gly Glu Phe Phe Tyr
    370                 375                 380

Cys Asn Thr Ser Gly Leu Phe Asn Ser Thr Trp Val Asn Gly Thr Ala
385                 390                 395                 400

Ser Ile Glu Asn Gly Thr Ile Thr Leu Pro Cys Arg Ile Lys Gln Ile
                405                 410                 415

Ile Asn Met Trp Gln Arg Val Gly Gln Ala Ile Tyr Ala Pro Pro Ile
            420                 425                 430

Gln Gly Val Ile Arg Cys Val Ser Asn Ile Thr Gly Leu Ile Leu Thr
            435                 440                 445

Arg Asp Gly Gly Asn Ser Asn Glu Asn Glu Thr Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Arg Arg
                485                 490                 495

Arg Val Val Glu Arg Glu Lys Arg Ala Val Thr Leu Gly Ala Val Phe
            500                 505                 510

Ile Gly Phe Leu Gly Thr Ala Gly Ser Thr Met Gly Ala Ala Ser Ile
            515                 520                 525

Thr Leu Thr Val Gln Ala Arg Lys Leu Leu Ser Gly Ile Val Gln Gln
    530                 535                 540

Gln Ser Asn Leu Leu Arg Ala Ile Glu Ala Gln Gln His Leu Leu Lys
545                 550                 555                 560

Leu Thr Val Trp Gly Ile Lys Gln Leu Gln Ala Arg Val Leu Ala Val
                565                 570                 575

Glu Arg Tyr Leu Arg Asp Gln Gln Leu Leu Gly Ile Trp Gly Cys Ser
            580                 585                 590

Gly Lys Leu Ile Cys Pro Thr Asn Val Pro Trp Asn Ser Ser Trp Ser
            595                 600                 605

Asn Lys Ser Leu Asp Glu Ile Trp Asp Asn Met Thr Trp Leu Gln Trp
    610                 615                 620

Asp Lys Glu Ile Ser Asn Tyr Thr Ile Lys Ile Tyr Glu Leu Ile Glu
625                 630                 635                 640

Glu Ser Gln Ile Gln Gln Glu Arg Asn Glu Lys Asp Leu Leu Glu Leu
                645                 650                 655

Asp Lys Trp Ala Ser Leu Trp Asn Trp Phe Asp Ile Ser Lys Trp Leu
            660                 665                 670
```

-continued

```
Trp Tyr Ile Lys Ile Phe Ile Met Ile Val Gly Gly Leu Ile Gly Leu
            675                 680                 685

Arg Ile Val Phe Ala Val Leu Ser Val Ile Asn Arg Val Arg Gln Gly
    690                 695                 700

Tyr Ser Pro Leu Ser Phe Gln Thr His Thr Pro Asn Pro Arg Gly Leu
705                 710                 715                 720

Asp Arg Pro Gly Arg Ile Glu Glu Gly Gly Glu Gln Asp Arg Gly
                725                 730                 735

Arg Ser Ile Arg Leu Val Ser Gly Phe Leu Ala Leu Ala Trp Asp Asp
            740                 745                 750

Leu Arg Asn Leu Cys Leu Phe Ser Tyr His Arg Leu Arg Asp Phe Ile
            755                 760                 765

Leu Ile Ala Ala Arg Thr Val Glu Leu Leu Gly His Ser Ser Leu Lys
            770                 775                 780

Gly Leu Arg Leu Gly Trp Glu Gly Leu Lys Tyr Leu Gly Asn Leu Leu
785                 790                 795                 800

Leu Tyr Trp Gly Arg Glu Leu Lys Ile Ser Ala Ile Asn Leu Leu Asp
                805                 810                 815

Thr Ile Ala Ile Ala Val Ala Gly Trp Thr Asp Arg Val Ile Glu Thr
            820                 825                 830

Val Gln Arg Leu Gly Arg Ala Ile Leu Asn Ile Pro Arg Arg Ile Arg
            835                 840                 845

Gln Gly Phe Glu Arg Ala Leu Leu
850                 855

<210> SEQ ID NO 3
<211> LENGTH: 4
<212> TYPE: PRT
<213> ORGANISM: Artificial sequence
<220> FEATURE:
<223> OTHER INFORMATION: two-cysteine mini-domain 1
<220> FEATURE:
<221> NAME/KEY: misc_feature
<222> LOCATION: (2)..(3)
<223> OTHER INFORMATION: Xaa can be any naturally occurring amino acid

<400> SEQUENCE: 3

Cys Xaa Xaa Cys
1

<210> SEQ ID NO 4
<211> LENGTH: 5
<212> TYPE: PRT
<213> ORGANISM: Artificial
<220> FEATURE:
<223> OTHER INFORMATION: two-cysteine mini-domain 2
<220> FEATURE:
<221> NAME/KEY: misc_feature
<222> LOCATION: (2)..(4)
<223> OTHER INFORMATION: Xaa can be any naturally occurring amino acid

<400> SEQUENCE: 4

Cys Xaa Xaa Xaa Cys
1               5

<210> SEQ ID NO 5
<211> LENGTH: 6
<212> TYPE: PRT
<213> ORGANISM: Artificial
<220> FEATURE:
<223> OTHER INFORMATION: two-cysteine mini-domain 3
<220> FEATURE:
```

```
<221> NAME/KEY: misc_feature
<222> LOCATION: (2)..(5)
<223> OTHER INFORMATION: Xaa can be any naturally occurring amino acid

<400> SEQUENCE: 5

Cys Xaa Xaa Xaa Xaa Cys
1               5

<210> SEQ ID NO 6
<211> LENGTH: 27
<212> TYPE: PRT
<213> ORGANISM: Influenza A virus H3 TMD

<400> SEQUENCE: 6

Asp Trp Ile Leu Trp Ile Ser Phe Ala Ile Ser Cys Phe Leu Leu Cys
1               5                   10                  15

Val Val Leu Leu Gly Phe Ile Met Trp Ala Cys
            20                  25
```